(12) United States Patent
Giambattista et al.

(10) Patent No.: US 6,986,760 B2
(45) Date of Patent: Jan. 17, 2006

(54) PEN NEEDLE AND SAFETY SHIELD SYSTEM

(75) Inventors: Lucio Giambattista, East Hanover, NJ (US); David De Salvo, Butler, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 4 days.

(21) Appl. No.: 10/191,714

(22) Filed: Jul. 9, 2002

(65) Prior Publication Data

US 2003/0014018 A1 Jan. 16, 2003

Related U.S. Application Data

(63) Continuation-in-part of application No. 10/072,691, filed on Feb. 7, 2002, now abandoned.
(60) Provisional application No. 60/222,454, filed on Jul. 25, 2001.

(51) Int. Cl.
  *A61M 5/00* (2006.01)
  *A61M 5/32* (2006.01)

(52) U.S. Cl. .................. 604/198; 604/195; 604/192; 604/110

(58) Field of Classification Search ......... 604/110–198, 604/201, 221, 241, 218, 263
See application file for complete search history.

(56) References Cited

U.S. PATENT DOCUMENTS

| | | | | |
|---|---|---|---|---|
| 5,169,392 A | | 12/1992 | Ranford et al. ............. | 604/198 |
| 5,201,708 A | * | 4/1993 | Martin ....................... | 604/110 |
| 5,201,721 A | | 4/1993 | Lee et al. ................... | 604/198 |
| 5,385,551 A | * | 1/1995 | Shaw .......................... | 604/110 |
| 5,415,645 A | | 5/1995 | Friend et al. ............... | 604/110 |
| 5,417,660 A | | 5/1995 | Martin ....................... | 604/110 |
| 5,417,662 A | | 5/1995 | Hjertman et al. ........... | 604/117 |
| 5,429,612 A | | 7/1995 | Berthier ..................... | 604/198 |

(Continued)

FOREIGN PATENT DOCUMENTS

| | | |
|---|---|---|
| WO | WO 92/19296 | 11/1992 |
| WO | WO 97/14455 | 4/1997 |
| WO | WO 02/09797 | 2/2002 |

*Primary Examiner*—Nicholas D. Lucchesi
*Assistant Examiner*—Roz Maiorino
(74) *Attorney, Agent, or Firm*—David H. Fortunato

(57) ABSTRACT

A safety shield system for a needle cannula of a pen needle injector or similar device, wherein a safety shield may be retracted from a first position enclosing the needle cannula to a second position exposing the needle cannula for injection. The safety shield system permits retraction of the safety shield during use, but extends the shield enclosing the needle cannula in a locked position following use. The shield system is utilized with a pen needle injector having a double-ended needle cannula mounted in a hub member received on an open end of the pen needle injector. The assembly is disposed of by removing the system and storing the assembly in the cup-shaped top cap enclosing the exposed end of the needle cannula within the cap. The top cap includes internal radial ribs preventing retraction of the shield prior to removing the top cap preventing inadvertently piercing the top cap during assembly. In addition, a bottom cap may be interlocked to the top cap to completely encompass the needle cannula, thereby ensuring safe disposal of the assembly.

28 Claims, 14 Drawing Sheets

U.S. PATENT DOCUMENTS

| | | | |
|---|---|---|---|
| 5,478,316 A | 12/1995 | Bitdinger et al. | 604/135 |
| 5,545,145 A | 8/1996 | Clinton et al. | 604/192 |
| 5,634,910 A | 6/1997 | Kanner et al. | 604/208 |
| 5,709,662 A | 1/1998 | Olive et al. | 604/135 |
| 5,829,589 A | 11/1998 | Nguyen et al. | 206/366 |
| 5,843,036 A | 12/1998 | Olive et al. | 604/136 |
| 5,873,462 A | 2/1999 | Nguyen et al. | 206/366 |
| 5,873,856 A | 2/1999 | Hjertman et al. | 604/117 |
| 5,941,857 A | 8/1999 | Nguyen et al. | 604/263 |
| 5,944,700 A | 8/1999 | Nguyen et al. | 604/263 |
| 5,951,530 A | 9/1999 | Steengaard et al. | 604/272 |
| 5,964,731 A | 10/1999 | Kovelman | 604/110 |
| 5,980,491 A | 11/1999 | Hansen | 604/157 |
| 5,984,906 A | 11/1999 | Bonnichsen et al. | 604/272 |
| 6,017,329 A | 1/2000 | Hake | 604/198 |
| 6,077,253 A | 6/2000 | Cosme | 604/263 |
| 6,379,337 B1 * | 4/2002 | Mohammad M. B. B. S. | 604/195 |
| 6,569,123 B2 * | 5/2003 | Alchas et al. | 604/192 |
| 2002/0004648 A1 | 1/2002 | Larsen et al. | 604/195 |

* cited by examiner

FIG · 14

PEN NEEDLE AND SAFETY SHIELD SYSTEM

FIELD AND BACKGROUND OF THE INVENTION

This patent application is a continuation-in-part of U.S. patent application Ser. No. 10/072,691, filed Feb. 7, 2002, now ABN, which in turn claims priority to U.S. Provisional Application Ser. No. 60/222,454, filed Jul. 25, 2001.

The present invention relates to an improved pen needle and safety shield system particularly, but not exclusively, adapted for pen injectors. The safety shield system in accord with aspects of this invention include a retractable generally tubular shield which is spring-biased to normally enclose the needle cannula of a pen needle dispenser, but which locks in the extended position enclosing the needle cannula following injection. Further, the double-ended needle cannula assembly may be safely nested in the cup-shaped cap following injection for disposal.

Hypodermic syringes are used to deliver selected doses of fluids including liquid medicaments, inoculations, etc. to patients. However, many applications using hypodermic needles are self-administered, including, for example, insulin, anti-histamines, et cetera. The required manipulation of a standard prior art hypodermic syringe can be inconvenient, particularly where the injection is self-administered in a public environment. Medication delivery pens or pen injectors have therefore been developed to facilitate self-administration of injections. A typical pen injector includes a generally tubular body portion resembling a fountain pen which receives a vial of fluid, such as insulin, anti-histamines, et cetera, having a pierceable closure, such as a rubber septum. The pen needle includes a hub generally having a double-ended needle cannula including a first end which extends into the body portion of the pen injector for piercing the closure of the vial and a second end used for self-injection of the fluid contained in the vial. The pen needle also generally includes a removable cup-shaped cap which encloses the second end of the needle cannula prior to use.

Various improvements in pen needles have been developed or proposed since their introduction, including adjustable injection length pen needles as disclosed in U.S. Pat. No. 5,944,700 assigned to the assignee of the present application and safety shield systems for such pen needles, wherein the shield is generally cup-shaped including an open end which receives the body portion of the pen needle and a generally closed end portion having a central opening which receives the second end of the needle cannula when the shield is retracted from a first position enclosing the second end of the needle cannula to a second position wherein the needle cannula is exposed for injection. The assembly may further include a spring that biases the shield to the normally enclosed first position prior to injection.

Various safety shield systems have also been developed or proposed by the prior art for conventional hypodermic syringes wherein a tubular shield is spring biased to enclose the needle cannula following injection and including safety shields which lock in the extended enclosed position following injection. Such safety shield systems for conventional hypodermic syringes are operated manually or are spring biased to extend the tubular shield and enclose the needle cannula following injection but all require additional action "active systems" such as force, to activate as compared to the standard injection process. Hand manipulated safety shield systems may include spiral or complicated channel-shaped tracks on an inside surface of the shield which guide the shield during extension of the shield to enclose the needle cannula and lock the shield in the extended position. However, such complicated track systems may not always be reliable.

A safety shield system for pen needles has not yet been developed wherein the shield initially encloses the second end of the needle cannula prior to use, permits retraction of the shield for self-administration of the fluid in the pen needle dispenser and then extends and locks the shield in the extended position enclosing the needle cannula following use. It would also be desirable to simplify the operation of the shield to eliminate manual manipulation or rotational movement of the shield from the retracted position to a locked extended position.

One concern with certain pen needle accessories, such as hidden needle adapters, has been potential needle sticks to the user during assembly of the accessory on the pen injector. Because the shield must be retractable for injection and the shield and cap assembly is typically threaded on the pen needle dispenser, the natural tendency of the user or patient is to press the cap toward the injector during assembly. This may cause the needle cannula to pierce the cap and possibly puncture the user during assembly. Another concern associated with pen needles has been the safe disposal of the hub and double-ended needle cannula. As will be understood, one end of the double-ended needle cannula may be enclosed in the cup-shaped cap; however, the other end is exposed following removal of the hub assembly from the pen injector.

The pen needle and safety shield system in accord with one aspect of this invention solves these problems by providing a safety shield which normally encloses the needle cannula prior to use, permits retraction of the safety shield during injection and automatically extends and locks the shield in the extended enclosed position following use. The pen needle of this invention also prevents retraction of the shield during assembly of the shield and needle cannula and hub assembly on the pen injector. Further, the improved safety shield system of this invention permits safe disposal of the hub and double-ended needle cannula assembly following removal from the pen injector.

SUMMARY OF THE INVENTION

As set forth above, the improved safety shield system in accord with one aspect of this invention is particularly but not exclusively adapted for pen injectors. That is, although the safety shield system of this invention is specifically designed for use with pen injectors of the type described herein, the safety shield system of this invention may also be used with other devices including conventional hypodermic needle fluid delivery systems. For ease of description, however, the safety shield system of this invention will now be described as a component of a pen injector. As set forth above, such pen injectors generally include a tubular body portion adapted to receive a conventional vial for dispensing a fluid, such as insulin, anti-histamines, et cetera. A conventional pen needle dispenser further includes a needle cannula hub assembly wherein the hub is generally cup-shaped including a tubular portion having an open end which threadably receives the tubular end portion of the pen injector and a closed end portion which receives and secures the needle cannula. The tubular portion of the hub may be threadably or otherwise attached to the tubular end portion of the pen injector. The needle cannula extends through the end portion of the hub and includes a first end portion which extends into the body portion of the pen injector for piercing the closure in the vial and an opposed second end portion used for injection of a patient, including self-injection.

Certain implementations of improved safety shield system include a generally tubular clip member preferably having a tubular body portion received around the tubular hub portion of the hub assembly and a plurality of spaced laterally projecting resilient fingers. The free ends of the resilient fingers are hook-shaped opening toward the body portion of the pen injector. The safety shield system further includes a generally tubular reciprocable shield having a first tubular portion surrounding the clip member and a second tubular portion normally surrounding the second end of the needle cannula. As described below, the shield is spring biased to normally extend the second portion of the shield around the needle cannula. The shield can also include a plurality of spaced axially extending inwardly opening channel-shaped tracks on an inner surface of the shield which receive the resilient fingers of the clip member. During reciprocal motion of the shield as described below, the axially extending channel-shaped tracks guide the shield from a first position, wherein the shield second portion surrounds the second end of the needle cannula, to a second position, wherein the second end of the needle cannula is exposed for injection of a patient. The safety shield system further includes a spring resiliently biasing the shield axially to normally extend the shield second portion to surround the second end of the needle cannula. Thus, during use of the pen injector, the health care worker or patient presses the end of the shield against the area to be injected, which retracts the shield to the second position against the force of the spring. In a preferred embodiment, the shield is cup-shaped including the first and second tubular portions described above and a generally closed end portion having a central opening which receives the second end of the needle cannula therethrough during injection. Following use, the spring automatically extends the shield to enclose the second end of the needle cannula.

The shield includes an opening spaced from but near the open end of the shield, and means is provided to prevent the free end of the resilient finger from being received in the opening during retraction of the shield from the first position enclosing the second end of the needle cannula to expose the needle cannula as described. Thus, the shield may be retracted to expose the second end of the needle cannula during injection, but the resilient finger will lock into the opening when the spring extends the shield to enclose the second end of the needle cannula following injection. The shield is thereby locked in the first position enclosing the second end of the needle cannula following injection. In one embodiment, wherein the free end of the resilient fingers are hook-shaped as described above, the hook-shaped portion of the finger is received through the opening and securely locks the shield in the closed position. In a preferred embodiment, each of the channel-shaped tracks include an opening which receives and secures each of the locking fingers. The improved safety shield system thus permits one retraction of the safety shield during injection and locks the safety shield to enclose the second end of the needle cannula following injection. Although various means may be utilized in accord with the invention to prevent receipt of the locking fingers in the openings during retraction of the safety shield to expose the needle cannula, one embodiment includes a resilient detent or finger portion in the tracks adjacent the opening which resiliently biases the fingers of the clip member inwardly, such that the resilient fingers of the clip member travel past the opening during retraction of the shield member to the second position as described above. Further, the resilient detents catch the hook-shaped end portions of the resilient fingers during extension of the shield, assuring locking of the shield in the extended position following injection. Another embodiment has the hook-shaped portion of the finger being larger than the opening such that the finger slides over the opening when the shield is moved to the second position. The openings include a chamfer which catch the hook-shaped portions of the fingers when the shield is returned to the first position.

The safety shield system further includes a removable cup-shaped cap which is received over the shield prior to use. As will be understood, the cap is then removed and the pen injector is ready for use as described above. However, the cap of the improved safety shield system of this invention may also be used to safely store and dispose of the double-ended needle cannula. As described above, the second end of the needle cannula is protected following injection by the safety shield which is locked in the extended position surrounding the second end of the needle cannula. The needle cannula and safety shield system may then be safely stored in the cap for disposal by removing the needle cannula and safety shield assembly from the pen injector and inserting the first end of the needle cannula into the cup-shaped cap which is configured and adapted to receive and store the assembly for safe disposal. That is, the first end of the needle cannula is then located in the cup-shaped cap preventing exposure to the needle cannula and the second end portion is safely enclosed by the safety shield which is locked in the extended position protecting the second end of the needle cannula. Another embodiment of the subject invention includes a top cap and a bottom cap which interlock with each other to completely encompass the needle cannula.

The safety shield system in accord with aspects of this invention thus provides reliable operation and protection from the needle cannula. In certain implementations, the generally tubular safety shield moves axially guided by the axially extending channel-shaped tracks as described above, thereby eliminating rotational movement of the shield or a complex track system. The tubular body portion of the clip member includes a plurality of spaced axially extending radially projecting ribs which are received in axially extending grooves in the tubular portions of the shield, assuring axial movement of the shield during retraction and extension of the shield as described above. The resilient fingers of the clip member include a U-shaped portion integrally connected to the tubular portion of the clip member and hook-shaped free end portions as described above. This configuration provides additional resiliency for the hook-shaped end portions of the fingers. Further, the U-shaped portion of the fingers preferably open toward the generally closed end of the shield and the spring includes a first end received in the U-shaped portions of the fingers and a second end biased against the generally closed end of the shield assuring reliable movement of the shield.

The pen needle and safety shield system of this invention also prevents retraction of the shield during assembly of the safety shield system on the pen injector. As set forth above, one problem with certain pen needles has been potential piercing of the cap during threaded assembly of the cap and shield assembly on the pen dispenser thereby exposing the user to puncture. The cap of the improved safety shield system includes a plurality of radially inwardly projecting ribs which are received in the axially extending grooves in the tubular portion of the shield against the axially projecting ribs on the clip member. The grooves in the tubular portion of the shield preferably extend through the sidewall of the shield from adjacent the generally closed end to the ribs. These internal ribs on the cap prevent retraction of the shield during threaded assembly of the cap and shield assembly on the pen injector, thereby preventing accidental puncture during assembly.

The pen needle and safety shield system in accord with aspects of this invention thus permits normal operation of the safety shield to retract the shield during injection and automatically extends and locks the shield following injection to prevent inadvertent contact with the second end of the needle cannula. Further, as described above, the needle cannula assembly may then be safely stored in the cup-shaped cap or cover for disposal wherein the first end of the needle cannula is located in the cup-shaped cover and the second end is protected by the safety shield. Other advantages and meritorious features of the pen needle and safety shield system of this invention will be more fully understood from the following description of the embodiments, the appended claims and the drawings, a brief description of which follows.

DETAILED DESCRIPTION OF THE PREFERRED EMBODIMENTS

Figure 1:
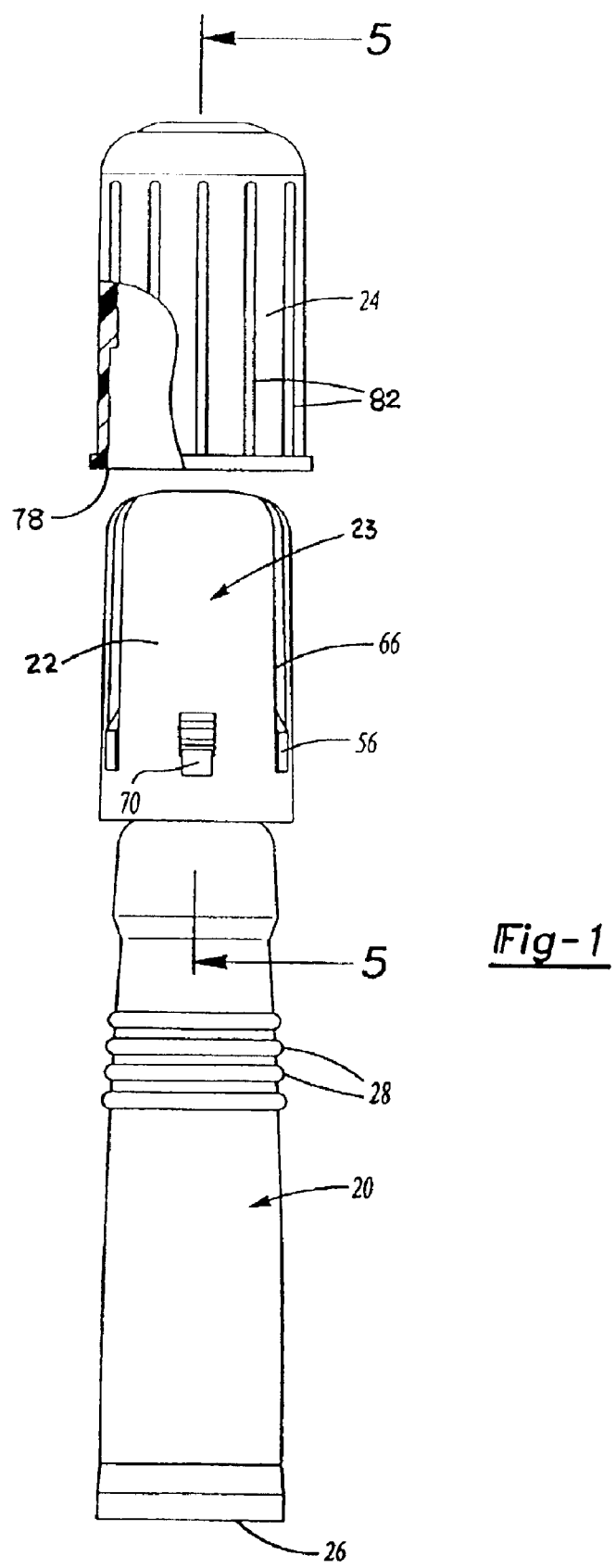
FIG. 1 is a side view of one embodiment of the pen needle and safety shield system in accord with an aspect of this invention with the cap removed.
Figure 2:
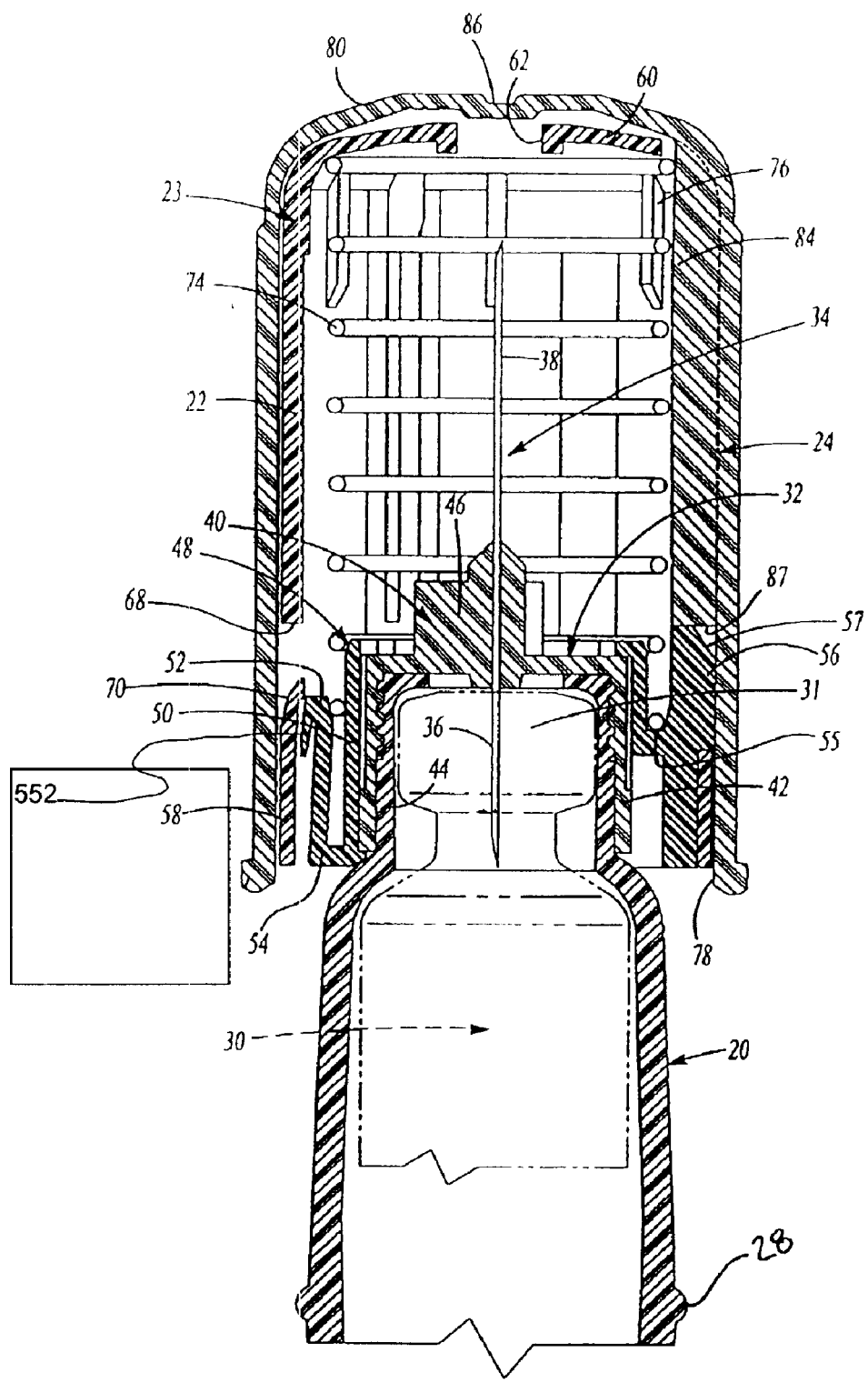
FIG. 2 is a partial cross-sectional view of the pen needle and safety shield system.

As set forth above, the improved safety shield system is particularly but not exclusively adapted for pen injectors, such as the pen needles available from Becton Dickinson and Company best shown at 20 in FIGS. 1 and 2. As will be understood, however, the safety shield system of this invention may also be used with other pen injectors of this general type and with conventional hypodermic syringes and drug delivery devices.

As described below, a safety shield 22 normally encloses a second end 38 of a needle cannula 34 as shown in FIG. 2 and a safety shield assembly 23 is enclosed by a cup-shaped cap 24 as shown in FIG. 1. The implementation of the pen injector 20 includes an open end 26 which may include external ribs 28 to facilitate gripping of the pen needle 20 by the user for threaded attachment of the safety shield assembly 23 to the pen injector 20 as described below. As shown in FIG. 2, the pen injector 20 receives a vial shown in phantom at 30 having a pierceable closure such as a rubber septum (not shown) in an open tubular end portion 31 of the vial. The pen injector 20 further includes a needle cannula and hub assembly 32 that includes the needle cannula 34 which extends through a hub member 40 to define a first end 36 that extends into the pen injector 20 to pierce the closure of the vial 30 or other container and the second opposed end 38 used for injection, including self-administration as described above. The hub member 40 includes a tubular rim portion 42 that is preferably threadably received on a tubular end portion 44 of the pen injector 20 and a central portion 46 that receives and secures the needle cannula 34. The needle cannula 34 includes a lumen or small passage therethrough for transferring fluid in the vial 30 to the user for self-injection or administration by a health care worker. The tubular rim portion 42 of the hub member 40 may include internal threads for threaded receipt of the hub member 40 on the externally threaded end portion 44 of the pen injector 20.

The safety shield system includes a generally tubular clip member 48 having a tubular body portion 50 which is received around the tubular rim portion 42 of the hub member 40, as shown in FIG. 2, and a plurality of laterally projecting resilient hook-shaped fingers 52. The clip member 48 may be formed of a resilient polymeric material, such as polypropylene, such that the fingers 52 are able to flex inwardly and resiliently flex outwardly as described below. Alternatively, the clip member 48 may be formed of a metal stamping or may be integrally formed with hub member 40. As shown in FIG. 2, for example, the fingers 52 are supported on a U-shaped portion 54 which further improves the resiliency of the fingers as they flex inwardly and spring outwardly. The clip member 48 further includes a plurality of circumferentially spaced radially extending ribs 56 which prevent rotational movement of the shield 22 and guide the shield 22 during axial movement of the shield 22 as described below.

Figure 3:
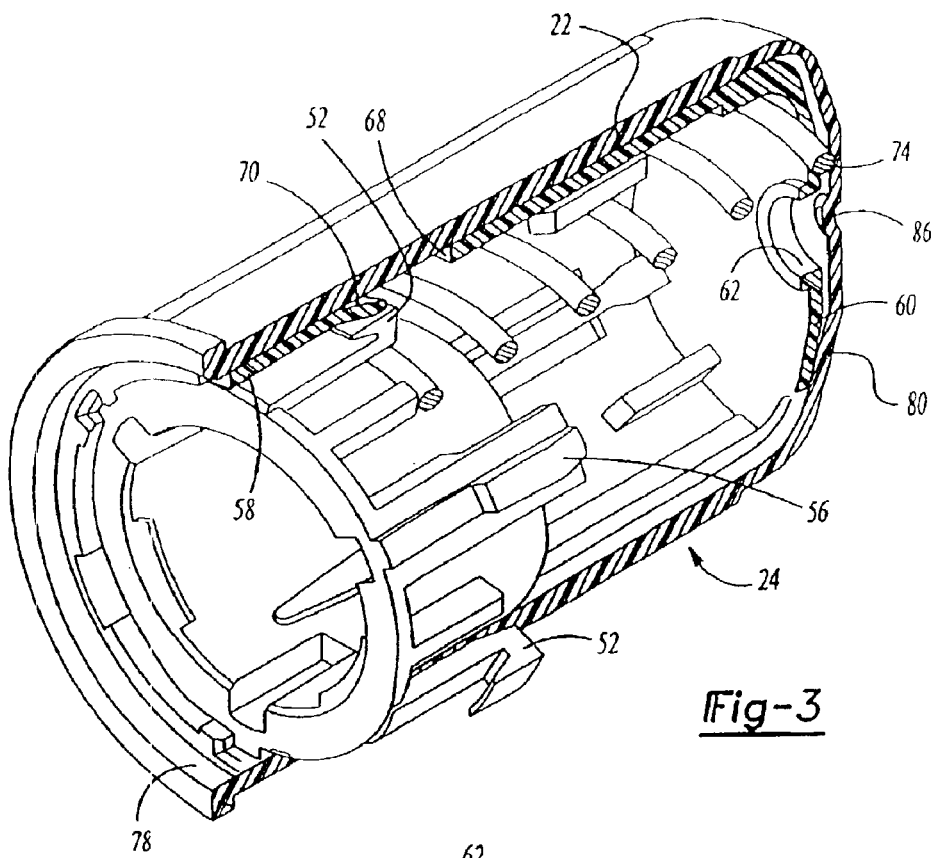
FIG. 3 is a side elevation partially cross-section of the safety shield assembly.
Figure 4:
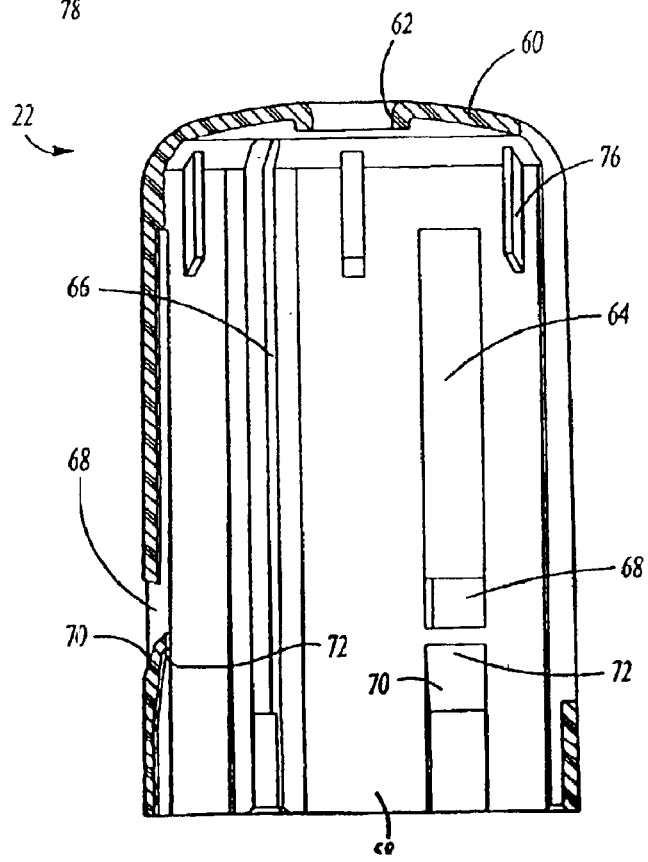
FIG. 4 is a side cross-sectional view of the safety shield.

Referring also to FIGS. 3 and 4, the safety shield 22 is generally tubular having an open end 58 and preferably including a generally closed end 60 having an axial opening 62 therethrough which receives the second end 38 of the needle cannula 34 as described below. The shield 22 further includes a plurality of circumferentially spaced longitudinally or axially extending channel-shaped tracks 64 in an internal surface of the tubular portion of the shield 22 that receives the hook-shaped fingers 52 and a plurality of circumferentially spaced axially extending slots or grooves 66 which receive the radial ribs 56 on the clip. As will be understood, the longitudinal axis of the safety shield 22 is coincident with the needle cannula 34. In one embodiment, the axial channel-shaped tracks 64 each include a radial opening 68 which is generally adjacent to but spaced from the open end 58 of the shield 22 in certain implementations of the invention. Each of the axial channel-shaped tracks 64 may include an inwardly projecting resilient integral tang or finger portion 70 adjacent the opening 68 closest to the open end 58 as seen in FIG. 4. The resilient tangs or finger portions 70 resiliently bias the hook-shaped fingers 52 inwardly and preferably include a ledge 72 releasably retaining the shield 22 in the extended position prior to injection as shown in FIG. 2 and further described below.

A coil spring 74 is biased between the clip member 48 and the generally closed end 60 of the shield 22, resiliently urging the shield 22 toward the extended position to enclose the second end 38 of the needle cannula 34, as shown in FIG. 2. The inside surface of the shield 22 includes a plurality of circumferentially spaced radially projecting ribs 76 that center the coil spring 74 in the shield 22. The cup-shaped cap 24 includes a closed end 80 and an open end 78. The open end receives the safety shield assembly 23 and needle cannula and hub assembly 32. In one embodiment, the internal surface of the cap 24 includes a plurality of radially projecting ribs 84 that extend axially from adjacent the closed end 80 to the ends of the radial ribs 56 and which prevent retraction of the safety shield 22 during assembly on the pen injector 20. The external surface of the cap 24 may also include ribs 82 to assist in gripping the cap 24 during assembly of the safety shield assembly 23 on the pen injector 20. The closed end 80 of the cap 24 also includes an inwardly projecting dimple 86 which is received in the opening 62 of the shield 22 centering the cap 24 on the shield 22. Other details of the embodiments of the safety shield assembly 23 will be discussed below in the description of the assembly and operation of the disclosed embodiment of the pen needle and safety shield system of this invention.

First, the operation of one implementation of the pen needle and safety shield system will now be described. One important advantage of the safety shield assembly 23 is that it may be preassembled with the needle cannula and hub assembly 32 and supplied to the patient or end user as an assembly ready for use. The first step taken by the patient or end user is then to attach this combined assembly to the pen injector 20 by threading the tubular rim portion 42 of the needle cannula and hub assembly 32 onto the tubular end portion 44 of the pen injector 20. As can be seen from FIG. 2, the internal ribs 84 on the cap 24 are aligned with the ribs 56 of the clip member 48 and prevent inadvertent depression or retraction of the safety shield assembly 23. Such depression or retraction could drive the second end 38 of the needle cannula 34 through the opening 62 of the shield 22 and puncture the cap 24, thereby exposing the end user to the needle cannula 34. The vial 30 may be previously loaded into the pen injector 20 and the open end 26 may be closed by an end cap (not shown), such that the threaded assembly results in piercing the first end 36 of the needle cannula 34 through the closure, such as a rubber septum, in the open end 31 of the vial 30 as the tubular rim portion 42 of the hub member 40 is threaded onto the rim portion 44 of the pen injector 20. Alternatively, the vial 30 may be inserted into the pen injector 20 following assembly.

Figure 5:
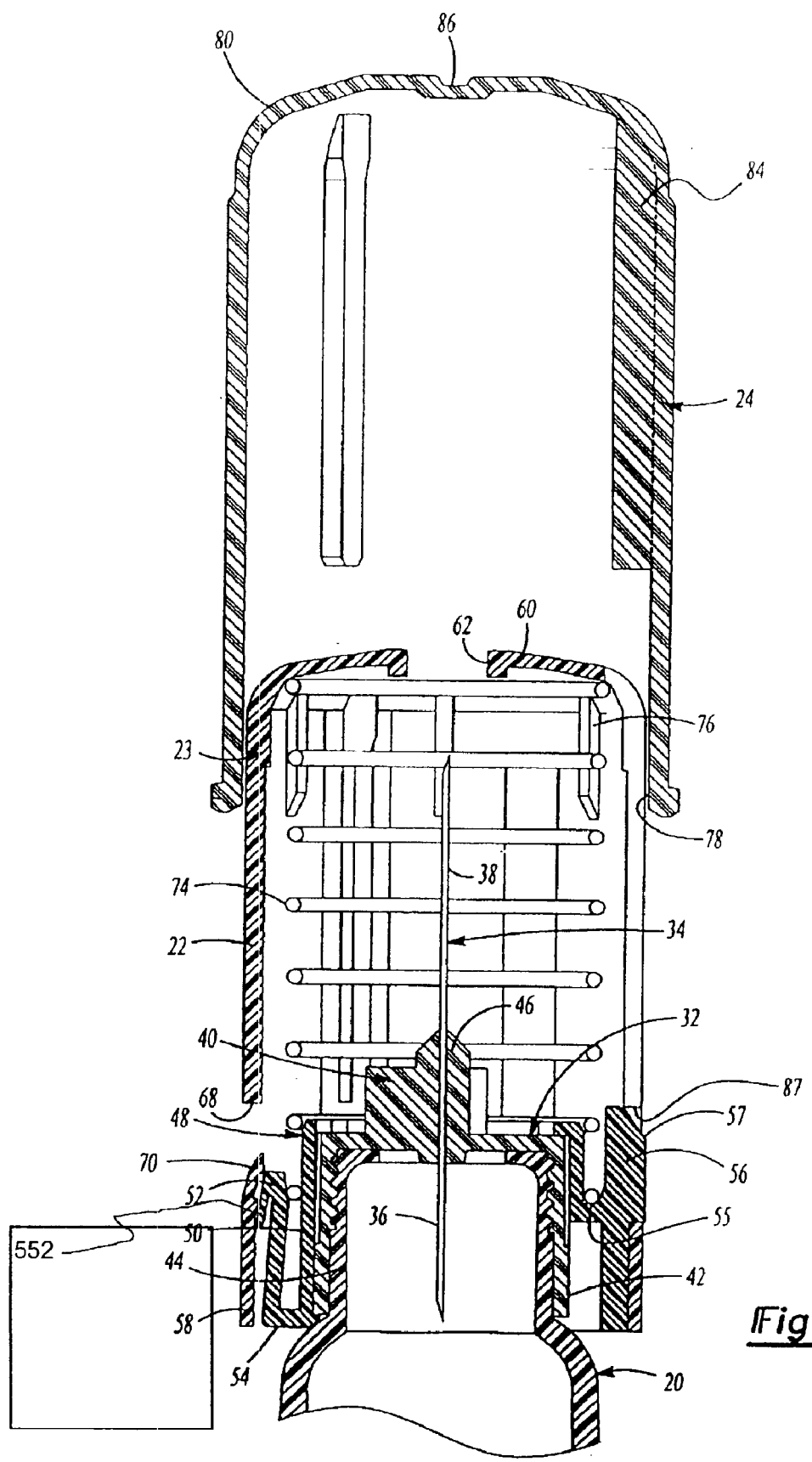
FIG. 5 is a partial side cross-sectional view of FIG. 1 in the direction of view arrows 5—5.

Once the vial is inserted in the pen injector 20, the cap 24 is removed from the assembly as shown in FIGS. 1 and 5. The pen needle and safety shield assembly is then ready for use.

Figure 6:
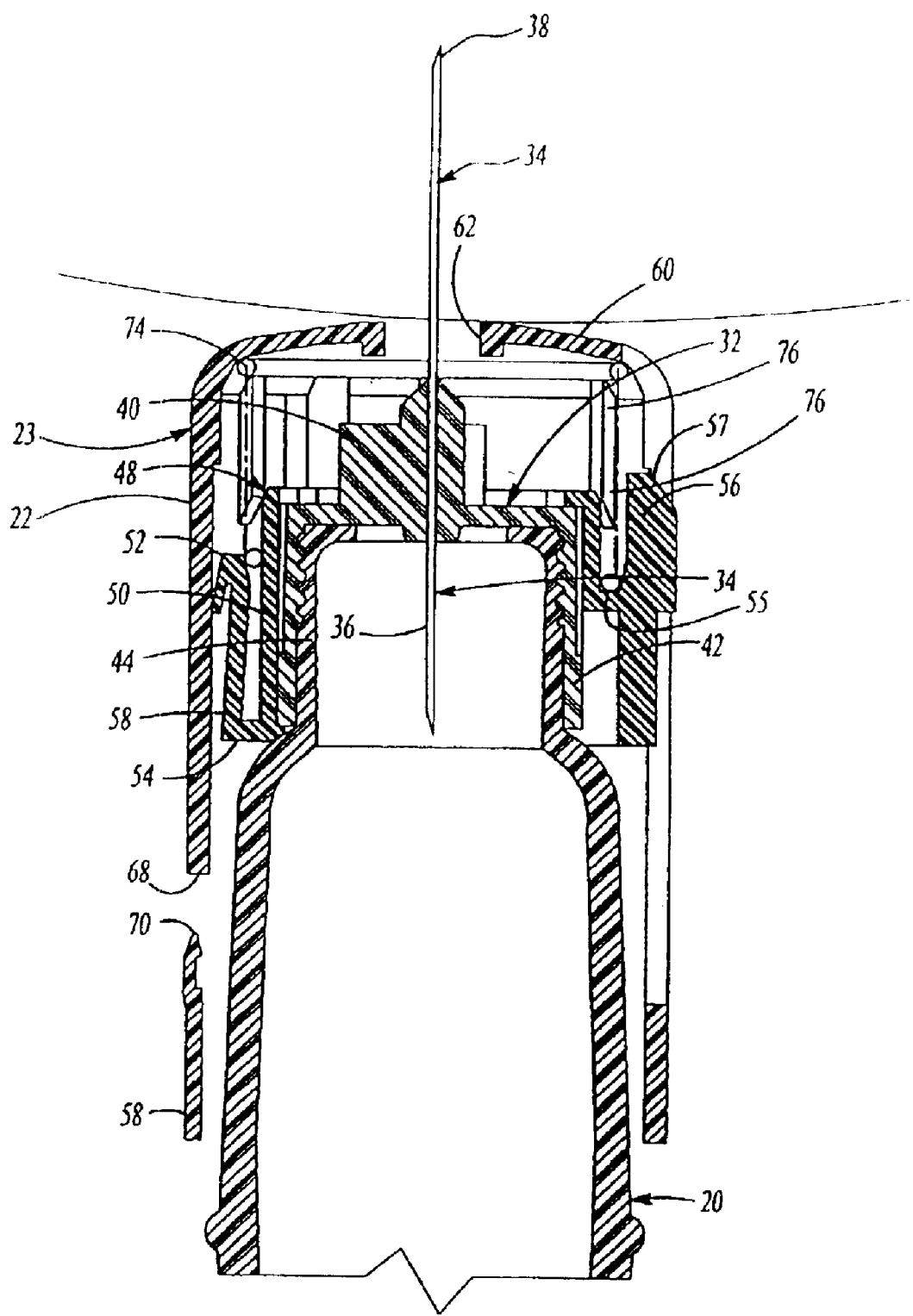
FIG. 6 is a partial cross-sectional view similar to FIG. 5 during use of the pen needle and safety shield assembly for injection.
Figure 14:
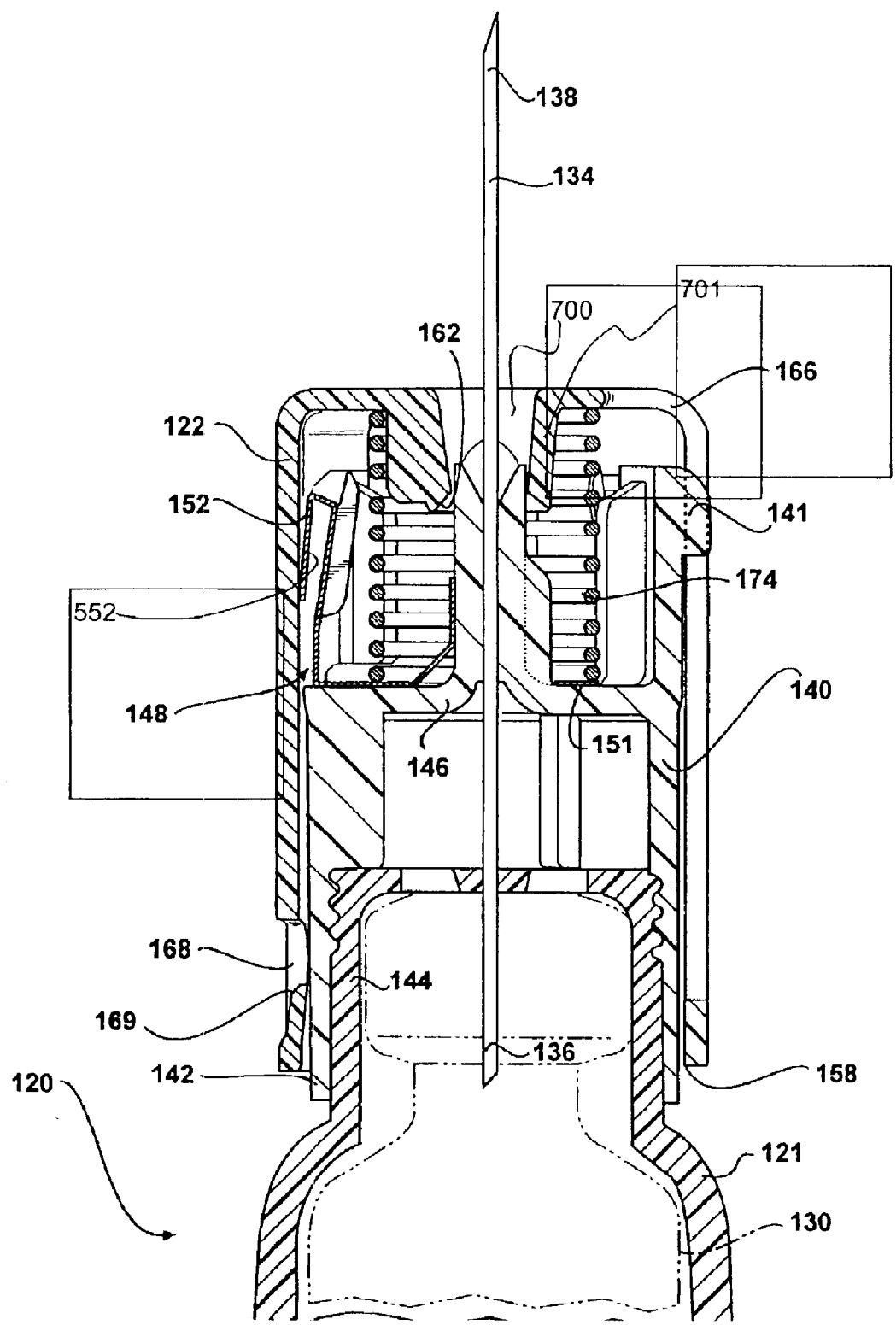
FIG. 14 is a partially cross-sectional view of the safety shield system of FIG. 9 during use of the pen needle for injection of a medicament.

As set forth above, the safety shield assembly 23 is particularly, but not exclusively, suitable for pen needle injectors typically used for self-administration of fluid or liquid drugs, vaccines or medicament, such as insulin, anti-histamines, et cetera. During use, the patient simply depresses the generally closed end 60 of the safety shield 22 against the body area to be injected, as shown in FIG. 6. As shown in FIGS. 2 and 5, the hook-shaped fingers 52 are releasably retained by the inwardly projecting tangs or finger portions 70 of the shield 22 preventing inadvertent retraction of the shield 22 and providing some resistance to movement of the shield 22 during injection which is considered an advantageous feature of this invention. Further, the fingers 52 are resiliently biased inwardly by the shield 22, such that retraction of the shield 22 when the generally closed end 60 of the shield 22 is pressed against the skin causes the fingers 52 to move over the openings 68 and move into the channel-shaped tracks 64 during initial retraction of the shield 22, exposing the second end 38 of the needle cannula 34 which is received through the opening 62 of the shield 22, resulting in injection of the patient. The top 552 of the fingers may be longer than the opening in the axial direction. Consequently, during actuation of the shield 22 (as seen in FIGS. 6 and 14), the top portion of the finger has passed the opening 68 before the end of the tip 552 moves into the opening. As such, the top portion of the finger does not contact the top of the opening during such actuation. Rotation of the shield 22 relative to the needle cannula and hub assembly 32 is prevented by the ribs 56 which follow the axial slots or grooves 66 assuring axial movement of the shield 22.

Figure 7:
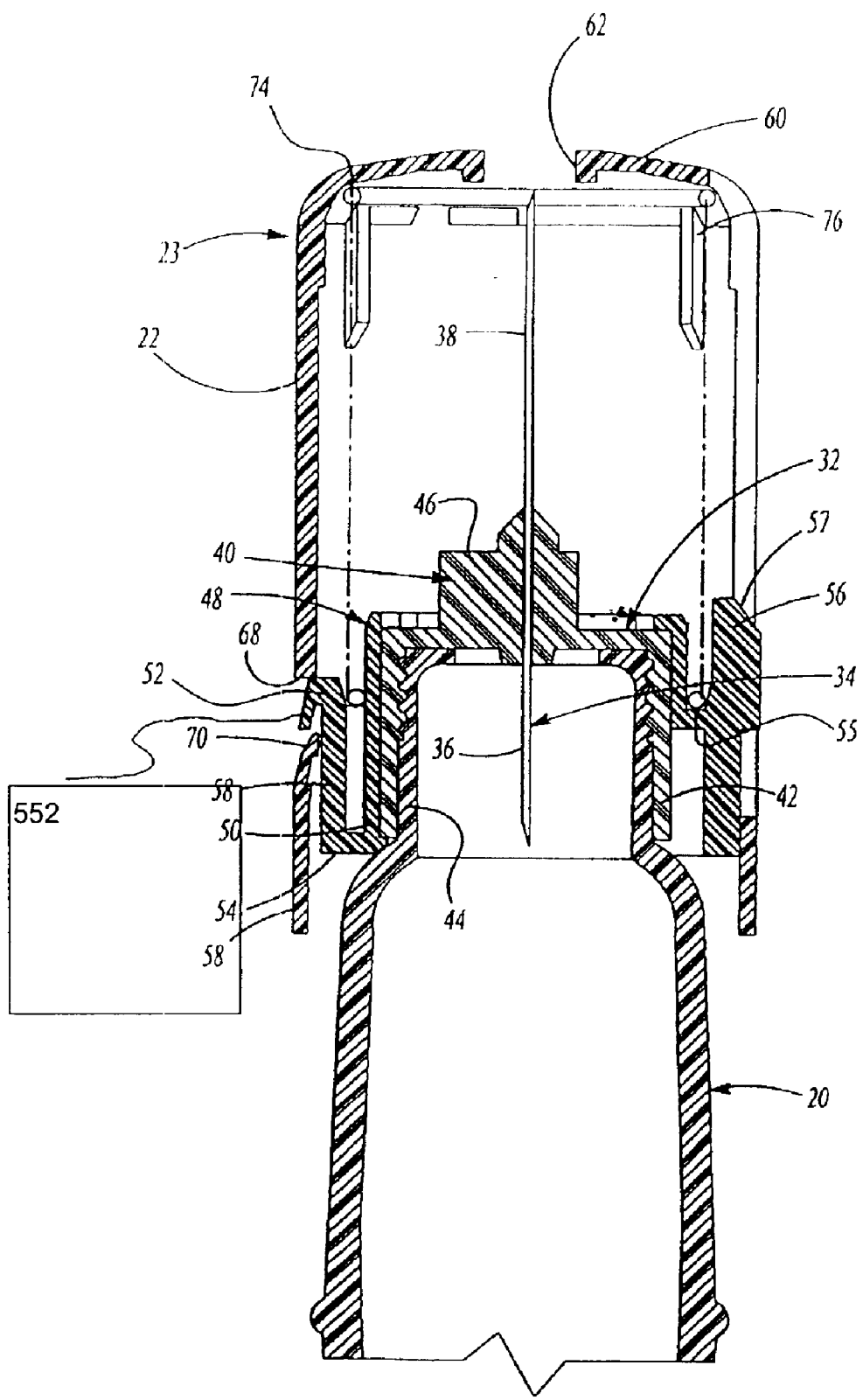
FIG. 7 is a partial side cross-sectional view similar to FIG. 6 following injection.

Following injection, the needle cannula 34 is withdrawn from the patient and the shield 22 is simultaneously extended by the coil spring 74, such that the second end 38 of the needle cannula 34 is never exposed. The shield 22 is extended axially as the needle cannula 34 is withdrawn because the hook-shaped fingers 52 move in the axial channel-shaped track 64 and the radial ribs 56 move through the slots or grooves 66. Upon full extension of the shield 22 to enclose the second end 38 of the needle cannula 34, the hook-shaped fingers 52 are received through the openings 68 and, in certain implementations of the invention, the hook-shaped portion is received around the inwardly projecting tang 70, locking the shield 22 in the extended position as shown in FIG. 7. The shield 22 cannot be retracted that is, moved downwards shown in FIG. 7 following injection to re-expose the second end 38 of the needle cannula 34.

Figure 8:
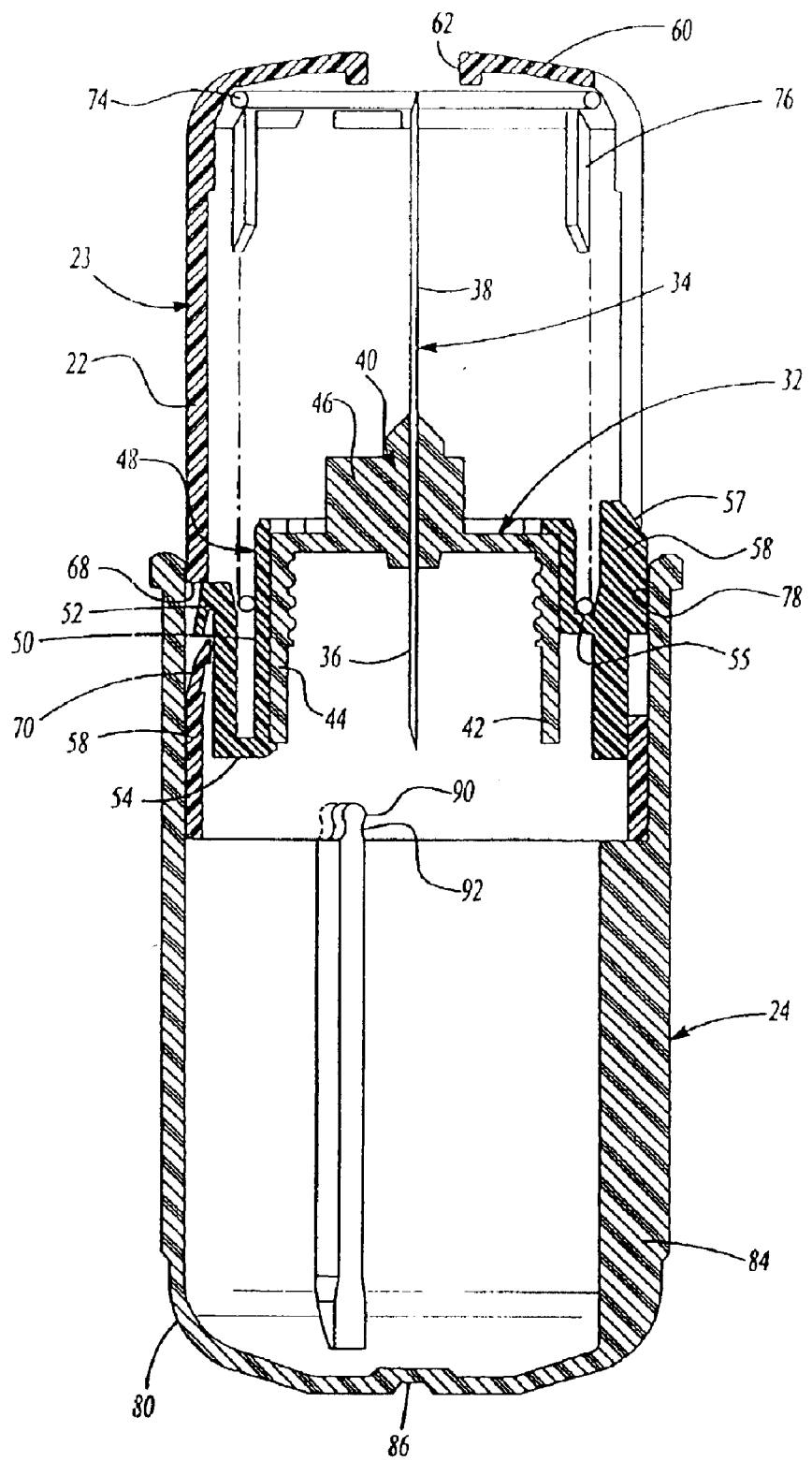
FIG. 8 is a side cross-sectional view of the safety shield system following removal from the pen injector and assembly for safe storage.

After use, the safety shield assembly 23 may be removed from the pen injector 20 by unthreading the tubular rim portion 42 of the hub member 40 from the threaded tubular end portion 44 of the pen injector 20 and safely disposed of directly into a sharps container or by reversing this assembly and inserting the assembly into the cup-shaped cap 24 as shown in FIG. 8. The first sharp end 36 of the needle cannula 34 is thus safely received in the cup-shaped cap 24 and the second end 38 of the needle cannula is protected by the safety shield 22, which is locked in the extended position, providing for safe disposal of the entire assembly. The internal ribs 84 of the cap 24 may be designed to provide an interference fit with the safety shield assembly 23, thereby preventing inadvertent removal of the assembly from the cap 24 and inadvertent exposure to either end of the needle cannula 34 following disposal. As shown in FIG. 8, one or more of the ribs 84 may include a ball-shaped end portion 90 which is received in a socket 92, securing the assembly in the cap 24 as shown in FIG. 8.

The improved safety shield assembly 23 thus provides several important advantages over the prior art, particularly pen injectors. First, the safety shield assembly 23 and cap 24 may be easily attached to the pen injector 20 without inadvertent retraction of the safety shield assembly 23 on the pen injector 20 and piercing of the cap 24, exposing the needle cannula 34 to the patient. This safety feature is provided by the radial ribs 56 on the hub member 40, which engage the internal ribs 84 of the cap 24 preventing retraction of the shield 22 during assembly. Upon removal of the cap 24, the pen injector 20 may be easily utilized for self-injection by the patient by depressing the generally closed end 60 of the safety shield 22 against the area to be injected without ever exposing the second end 38 of the needle cannula 34 to view. Following injection, the safety shield 22 is automatically extended by the spring 74 to enclose the second end 38 of the needle cannula 34 and locked in the extended position by the resilient fingers 52 which extend into the openings 68 through the channel-shaped tracks 64. The hook-shaped fingers 52 also lock over the resilient integral tangs 70. Following use, the safety shield assembly 23 and needle cannula and hub assembly 32 may be easily removed from the pen injector 20 by unthreading the tubular rim portion 42 of the hub member 40 from the tubular end portion 44 of the pen injector 20, reversing the assembly, and inserting the first end 36 of the needle cannula 34 into the cap 24, providing for safe disposal of the assembly wherein both ends of the double ended needle cannula 34 are safely enclosed, preventing inadvertent contact with the needle cannula 34.

As set forth above, the needle cannula and hub assembly 32 is assembled in the safety shield assembly 23 prior to receipt by the end user, wherein the hook-shaped fingers 52 are releasably retained by the ledge 72 of the inwardly projecting tangs 70 during assembly of the shield 22 on the clip member 48. The cap 24 is assembled on the shield 22 by disposing the inwardly projecting ribs 84 of the cap 24 into the slots 66 in the shield 22 as best shown in FIG. 1, wherein the end portions 87 of ribs 84 engage the ends of the radial rib portions 56 as best shown in FIG. 2. The radial ribs 56 in this embodiment include a chamfered end 57 which guides the ribs 56 into the slot 66 and the radial ribs 56 are connected to the tubular body portion by web portions 55. Further, the coil spring 74 is received between the radial ribs and the tubular body portion 50 against the web portion 55 as shown in FIG. 2. The radial ribs 56 may thus be resiliently flexed inwardly during assembly. As set forth above, the clip member 48 may be formed of a resilient polymeric material, such as polypropylene or formed of a metal stamping. All of the components of the safety shield assembly 23 and the cap 24 are preferably formed of a sterilizable material including a polymeric material which can be injection molded. Thus, a suitable material for the cap 24, shield 22 and clip member 48 is a sterilizable polypropylene.

Having described one embodiment of the pen needle and safety shield system of this invention, it will be understood that various modifications may be made to the disclosed embodiment within the purview of the appended claims. For example, other locking means for locking the shield 22 in the extended position following injection may be utilized. Further, locking means may be provided within the cap 24 for locking the safety shield assembly 23 within the cap 24 following removal of the safety shield assembly 23 from the pen injector 20 and storage of the assembly in the safety cap 24 as shown in FIG. 8, including interlocking ribs, etc. Further, certain improved features of the safety shield system of this invention may be utilized with conventional pen needle and shield assemblies, including, for example, the radial ribs 84 on the internal surface of the cap 24 which prevent depression or retraction of the shield 22 during assembly of the safety shield 22 and cap 24 on the pen injector 20 as described above.

Figure 9:
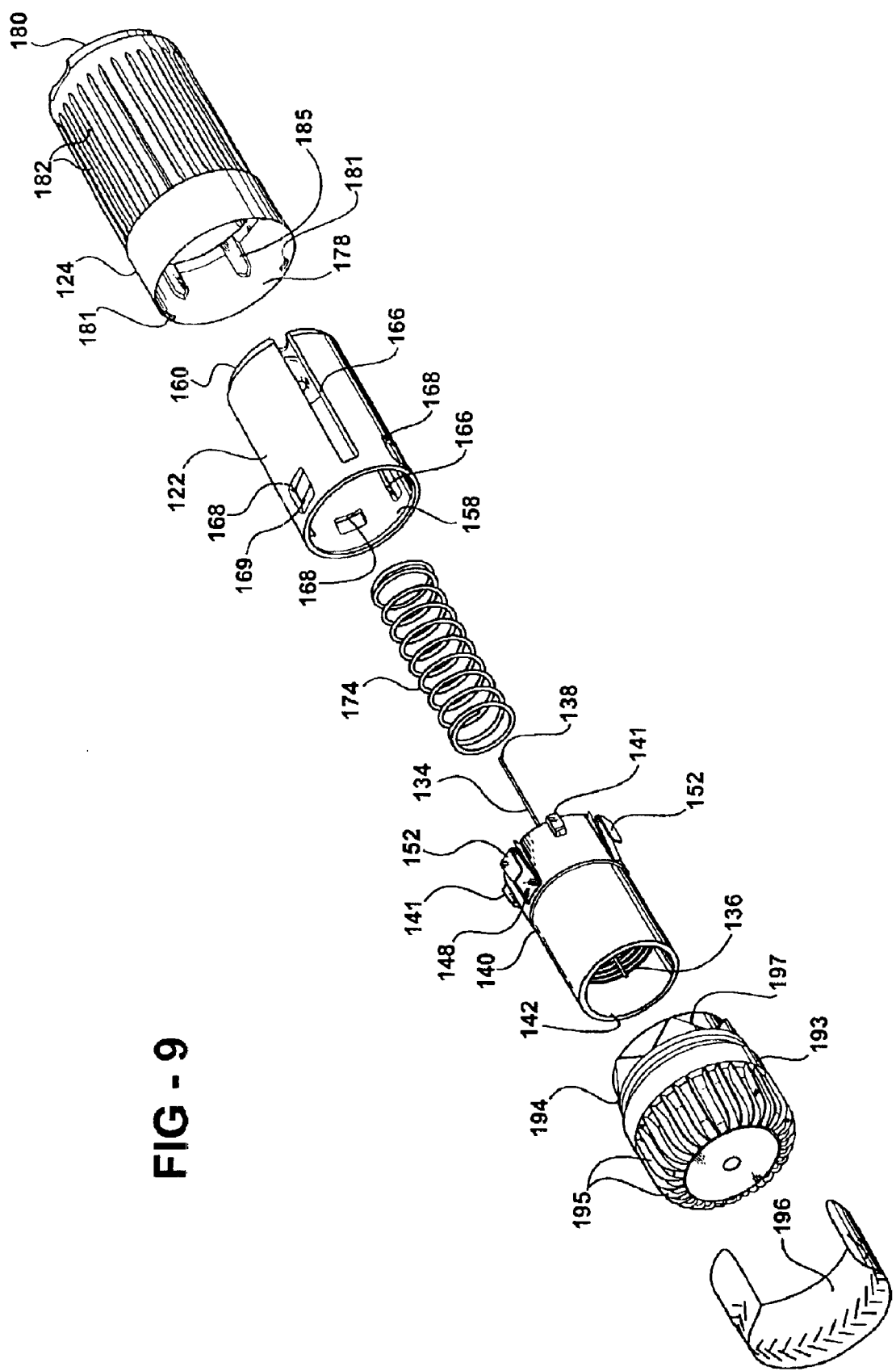
FIG. 9 is an exploded perspective view of another embodiment of the safety shield system.
Figure 10:
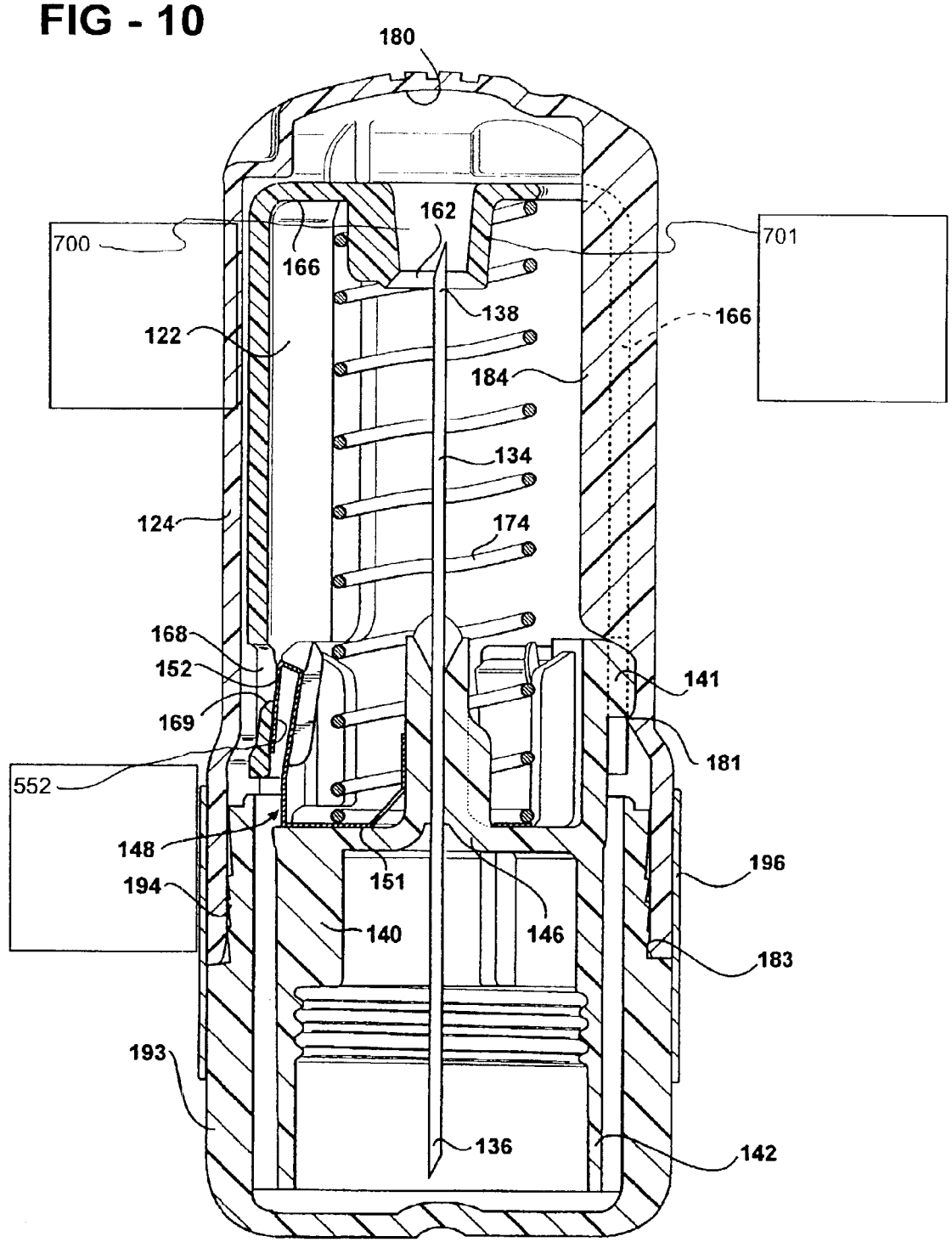
FIG. 10 is a partially cross-sectional view of the safety shield system of FIG. 9.
Figure 11:
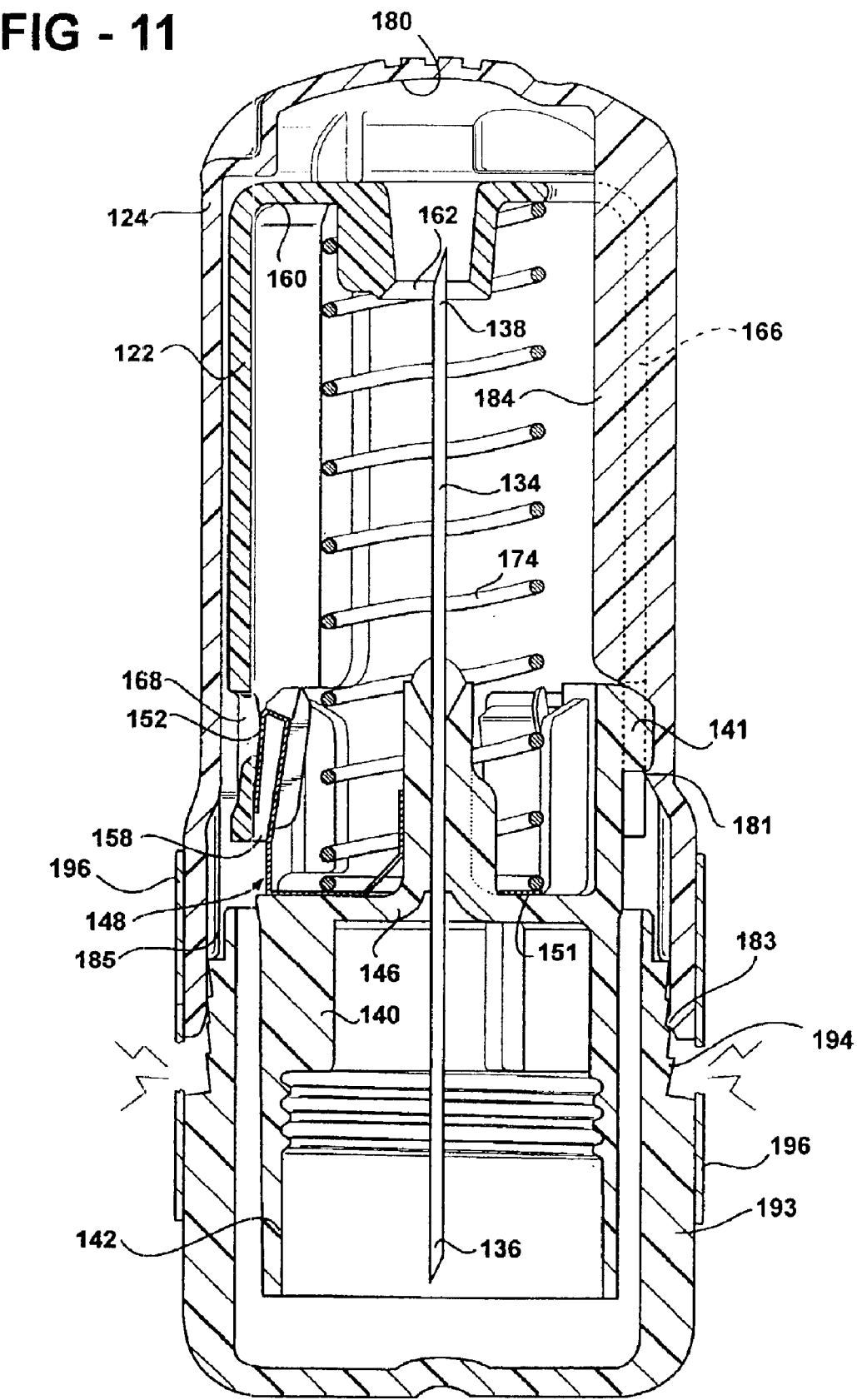
FIG. 11 is a partially cross-sectional view of the safety shield system of FIG. 9 illustrating a bottom cap being partially detached from a top cap.

Referring now to FIGS. 9–15, another implementation of the safety shield system is shown, in which, generally like numerals increased by one hundred indicate like or corresponding parts throughout the several views. FIGS. 9–11 illustrate the safety shield system per se and FIGS. 12–15 illustrate the safety shield system mounted to a pen injector 120. As shown in FIGS. 12–15, the pen injector 120 includes a body portion 121 for receiving a container 130, such as a vial 130, having fluid disposed therein.

The safety shield system includes a hub member 140 removably mounted to the body portion 121. The hub member 140 includes a tubular rim portion 142 which is preferably threadably received on a tubular end portion 144 of the pen injector 120. The hub member 140 also includes at least one radially extending rib 141 and a central portion 146 which receives and secures a needle cannula 134. In particular, the needle cannula 134 is mounted to and extends through the hub member 140. Specifically, the needle cannula 134 has a first end 136 extending into the body portion 121 for fluid communication with the container 130 and a second end 138 extending away from the body portion 121 for injection and transfer of the fluid from the container 130 to a user. As discussed above, the needle cannula 134 includes a lumen or small passage therethrough for transferring fluid in the vial 130 to the user for self-injection or administration by a health care worker.

Referring also to FIGS. 9–11, the safety shield 122 system includes a clip member 148 mounted to the hub member 140 and having at least one laterally projecting resilient finger 152. Preferably, the clip member 148 includes a plurality of spaced laterally projecting resilient fingers 152. Each of the resilient fingers 152 include a hook-shaped end portion. The clip member 148 may be formed of a metallic material and includes a common base 151 with each of the resilient fingers 152 extending from the base 151. The base 151 is in turn fastened to the central portion 146 of the hub member 140. Alternatively, the clip member may be formed of other materials or integrally formed with the hub. The fingers 152 are able to flex inwardly and resiliently flex outwardly as described below.

A shield 122 is moveably mounted to the clip member 148 between a first position surrounding the second end 138 of the needle cannula 134, see FIGS. 10–13, and 15, and a second position exposing the second end 138 of the needle cannula 134, see FIG. 14. The shield 122 is generally cup-shaped having an open end 158 received around the clip member 148 and a generally closed end 160 having a central opening 162 therethrough receiving the second end 138 of the needle cannula 134 as described below. The shield 122 includes at least one opening 168 and preferably a plurality of openings 168 for receiving the fingers 152. The openings 168 extends through a side wall of the shield 122 for receiving the hook-shaped end portions of the fingers 152 therethrough to lock the shield 122 in the first position surrounding the needle cannula 134 (shown in FIG. 15). Each of the hook-shaped end portions of the fingers 152 preferably open toward the shield 122 for easy insertion into the openings 168. In particular, the shield 122 is first retracted to the second position to expose the needle cannula 134, see FIG. 14, and then extended to the first position surrounding the needle cannula 134 where the fingers 152 now lock the shield 122 in the first position to prevent further exposure of the needle cannula 134, see FIG. 15.

In this embodiment of the subject invention, each of the hook-shaped end portions of the fingers 152 are larger than the corresponding openings 168 in the shield 122 such that the resilient fingers 152 initially slide over the openings 168 when the shield 122 is retracted to the second position. In particular, the hook-shaped end portions of the fingers 152 are longer than the openings 168 in the shield 122. The openings 168 each include a chamfer 169 with the fingers 152 first engaging the chamfer 169 and then extending into the openings 168 when the shield 122 returns to the first position from the second position.

Figure 13:
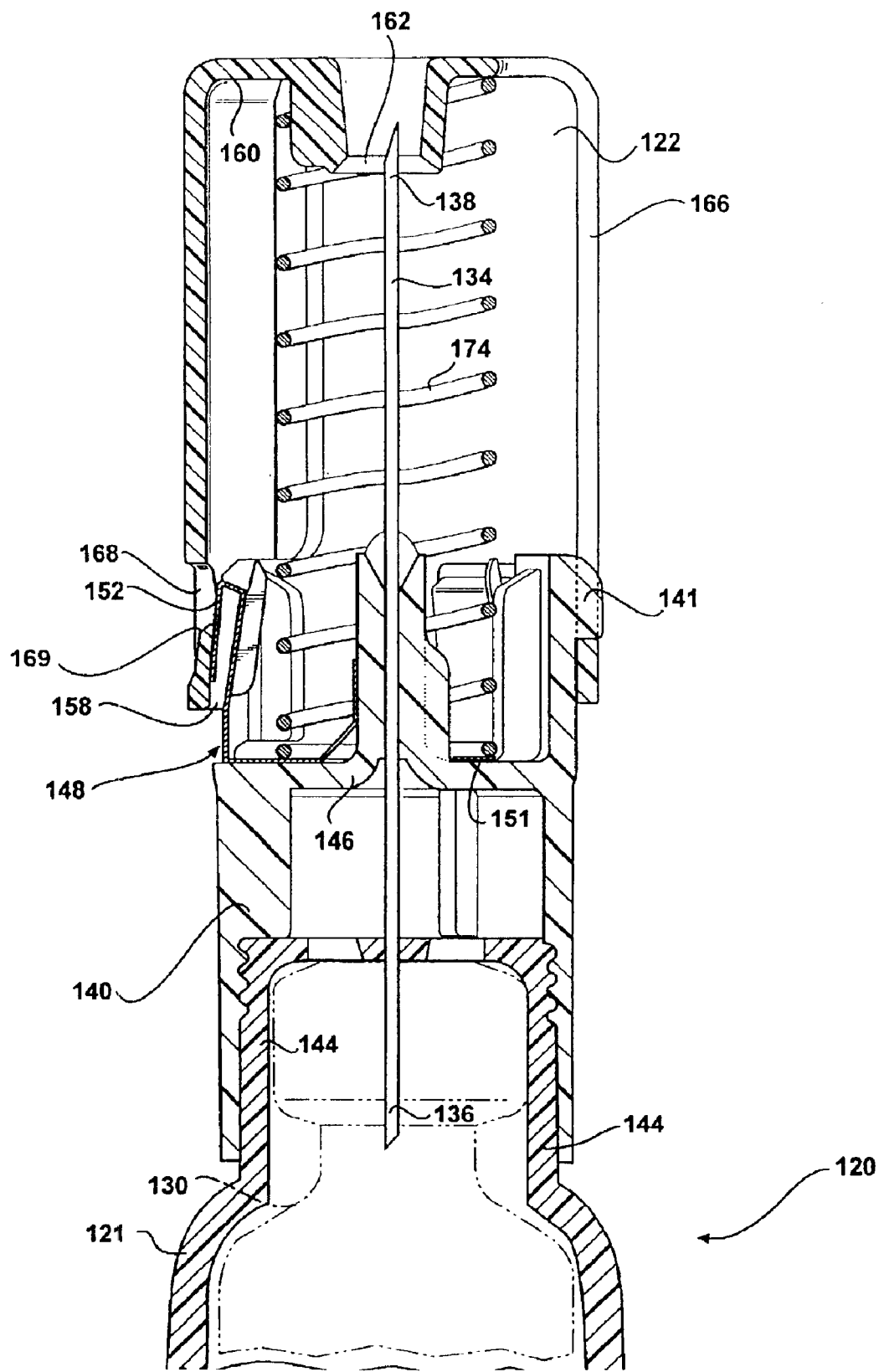
FIG. 13 is a partially cross-sectional view of the safety shield system of FIG. 9 mounted to the pen needle and having the top cap removed therefrom.

As seen, for example, in FIG. 13, the second end of the needle cannula is disposed within a channel 700 formed by a guide 701. As a result, the needle cannula is disposed within the opening 162, whether the tip of the needle is exposed or not. As the shield is retracted, the guide prevents the needle tip from catching on the portions of the shield adjacent to the opening 162.

The shield 122 further includes at least one radial groove 166 with the radially extending rib 141 of the hub member 140 being disposed within the groove 166 to prevent rotation of the shield 122 relative to the clip member 148. In the preferred embodiment, the shield 122 includes a plurality of spaced radial grooves 166 and the hub member 140 includes a plurality of spaced radially extending ribs 141 with a corresponding rib 141 disposed within each groove 166 to prevent rotation of the shield 122 relative to the clip member 148.

The safety shield 122 system further includes a spring 174 disposed within the shield 122 for continuously biasing the shield 122 toward the first position. Preferably, the spring 174 is a spiral spring having one end abutting the common base 151 and an opposed end biased against the generally closed end 160 of the shield 122.

As shown in FIGS. 9–12, a removable cup-shaped top cap 124 is also provided in this embodiment for initially being received over the shield 122. The top cap 124 includes an open end 178 which receives the hub member 140 as described below and a closed end 180. An internal surface of the cup-shaped top cap 124 includes inwardly projecting ribs 184 which are disposed within the grooves 166 of the shield 122. The ribs are designed to align with ribs 141 of the hub member 140 to prevent actuation during assembly. The shield 122 cannot be accessed when the top cap 124 is installed such that the shield 122 cannot retract relative to the hub member 140 when the top cap 124 is received over the shield 122. An external surface of the top cap 124 may also include ribs 182 to assist in gripping the top cap 124 during assembly of the shield system on the pen injector 120. The top cap 124 also includes first 181 and second 183 internal tabs. The first internal tabs 181 form an undercut which engages the ribs 141 of the hub member 140 to secure the top cap 124 to the hub member 140 and provide a degree of resistance during removal of the top cap 124 from the hub member 140. The top cap 124 further includes a first camming surface 185, the purpose of which will be discussed in detail below.

As shown in FIGS. 9–11, a removable cup-shaped bottom cap 193 is provided for this embodiment wherein the bottom cap 193 is likewise initially received over the hub member 140 opposite the top cap 124. The bottom cap 193 preferably interengages the top cap 124 when the top cap 124 is received over the shield 122 and the bottom cap 193 is received over the hub member 140 to completely surround the needle cannula 134. The interengagement between the top cap and the bottom cap forms a sterile barrier. The second internal tab 183 of the top cap 124 engages an annular notch 194 in the bottom cap 193 to secure the bottom cap 193 to the top cap 124 and provide a degree of resistance during removal of the bottom cap 193 from the top cap 124. The bottom cap 193 also includes a plurality of external ribs 195 for allowing a user to easily grip the bottom cap 193. Further, a frangible label 196 is at least partially adhered over both the top 124 and bottom 193 caps at the interface of the top 124 and bottom 193 caps. The frangible label 196 assists a user in identifying whether the bottom cap 193 has been separated from the top cap 124.

As with the top cap 124, the bottom cap 193 includes a second camming surface 197, best shown in FIG. 9. The first 185 and second 197 camming surfaces abut each other during rotation of the bottom cap 193 relative to the top cap 124 such that the bottom cap 193 simultaneously moves axially away from the top cap 124 during this rotation. In the embodiment shown, the first camming surface 185 is a plurality of inwardly facing ridges extending from the internal surface of the top cap 124 and the second camming surface 197 is a plurality of angled notches. During operation, the ridges abut the notches when the bottom cap 193 is interengaged with the top cap 124 such that during rotation of the bottom cap 193 relative to the top cap 124 the ridges ride along the angled notches to simultaneously move the bottom cap 193 axially away from the top cap 124.

The operation of this alternative embodiment of the pen needle 120 and safety shield system will now be described in greater detail. As with the embodiment of FIGS. 1–8, one important advantage of the safety shield system is that the safety shield system may be preassembled and supplied to the patient or end user as an assembly ready for use.

The first step by the patient or end user is to break the frangible label 196 by rotating the bottom cap 193 relative to the top cap 124, see FIG. 11. As mentioned above, the bottom cap 193 includes the second camming surface 197 which engages the first camming surface 185 on the top cap 124. The bottom cap 193 therefore axially separates from the top cap 124 as the bottom cap 193 is rotated thereby exposing the tabular rim portion 142 of the hub member 140 and the second end 138 of the needle cannula 134. The bottom cap 193 is then set aside for future use.

Figure 12:
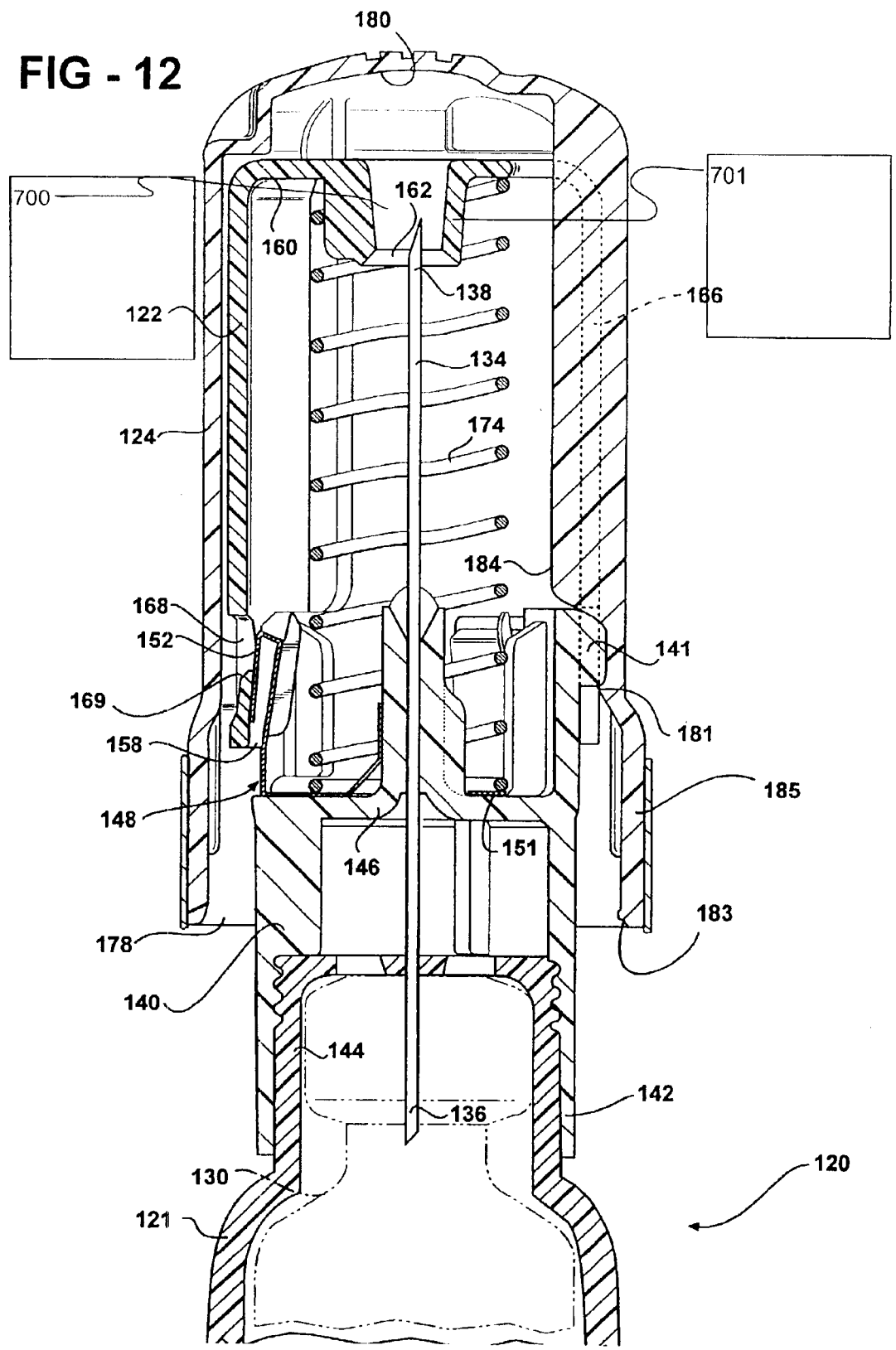
FIG. 12 is a partially cross-sectional view of the safety shield system of FIG. 9 mounted to a pen needle.

Referring to FIG. 12, the hub member 140 can now be attached to the pen injector 120 by threading the tubular rim portion 142 of the hub member 140 on the tubular end portion 144 of the pen injector 120. As can be seen from FIG. 12, the internal ribs 184 on the top cap 124, which are aligned with and about the ribs 141 of the hub member 140 and are disposed within the grooves 166 of the shield 122, prevent inadvertent depression or retraction of the shield 122 which could drive the second end 138 of the needle cannula 134 through the opening 168 of the shield 122 and puncture the top cap 124, which would expose the end user to the needle cannula 134. The vial 130 may be previously loaded into the pen injector 120 and the open end may be closed by an end cap (not shown), such that the threading assembly results in piercing the first end 136 of the needle cannula 134 through the closure, such as a rubber septum, in the open end of the vial 130. Alternatively, the vial 130 may be inserted into the pen injector 120 following assembly.

Figure 15:
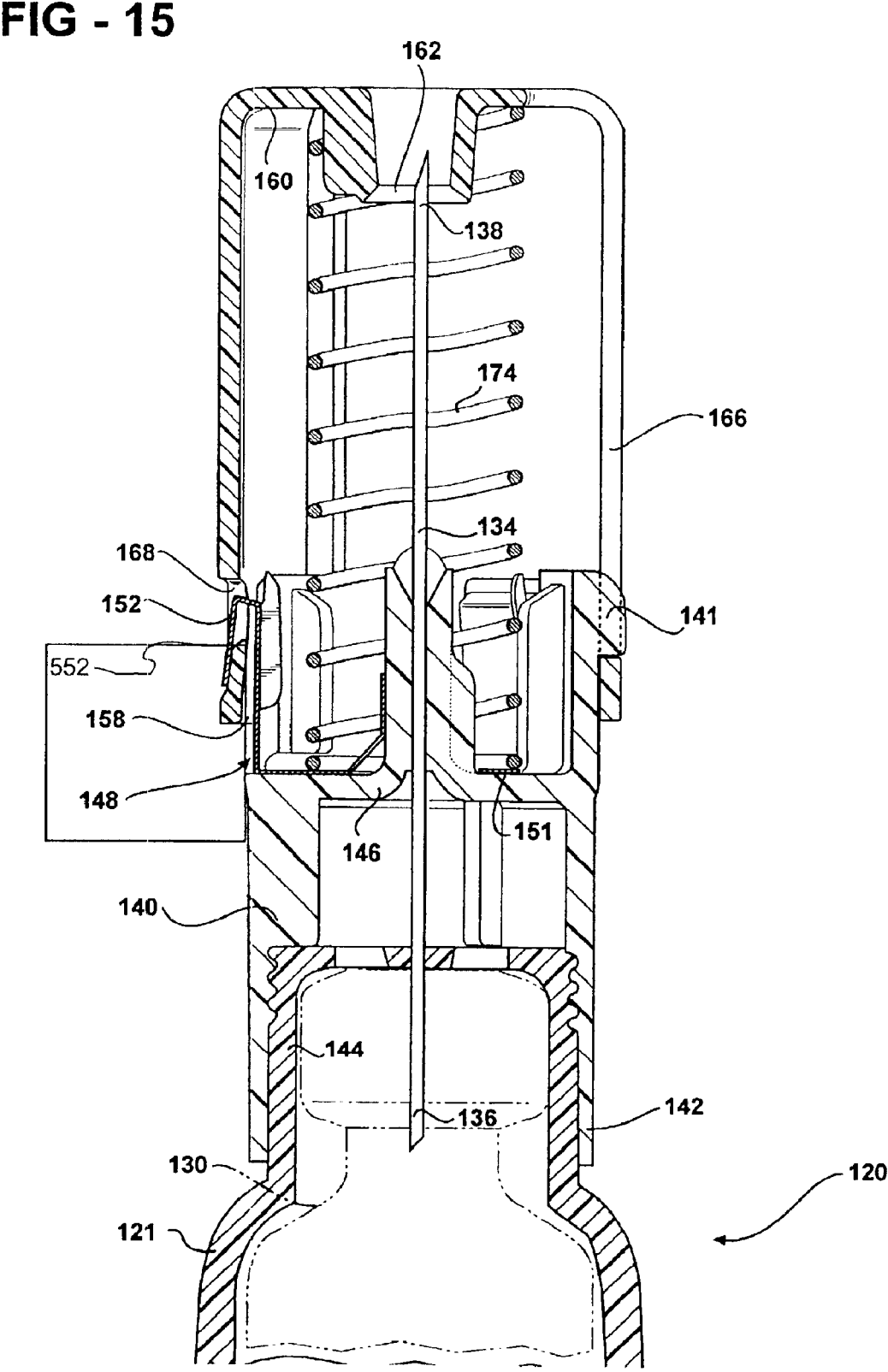
FIG. 15 is a partially cross-sectional view of the safety shield system of FIG. 9 following injection.

With the vial in place, the top cap 124 is removed from the assembly as shown in FIGS. 13–15 and set aside for future use. The safety shield system is then ready for use.

As set forth above, the safety shield system is particularly, but not exclusively, suitable for pen injectors 120 typically used for self-administration of fluid or liquid drugs, vaccines or medicament, such as insulin, anti-histamines, et cetera. During use, the patient simply depresses the generally closed end 160 of the shield 122 against a body area to be injected and actuates the pen injector. Referring to FIG. 14, this depression moves the shield 122 into the second position and allows the second end 138 of the needle cannula 134 to pass through the opening 168 in the shield 122 such that this end of the needle cannula 134 can be injected into the user.

During the movement of the shield 122 to the second position, the larger fingers 152 slide over the openings 168 and are resiliently biased inwardly. Preferably, the tips 652 of the fingers are longer than the openings 168 to prevent engagement of the finger to the opening during actuation. Rotation of the shield 122 relative to the hub member 140 is prevented by the ribs 141 which follow the axial slots or grooves 166 assuring axial movement of the shield 122.

Following injection, the needle cannula 134 is withdrawn from the patient and the shield 122 is simultaneously extended by the coil spring 174, such that the second end 138 of the needle cannula 134 is never exposed. Upon full extension of the shield 122 to enclose the second end 138 of the needle cannula 134, the hook-shaped end portions of the fingers 152 engage the chamfers 169 and are received through the openings 168 locking the shield 122 in the extended first position as shown in FIG. 15. That is, the shield 122 cannot be retracted following injection to expose the second end 138 of the needle cannula 134.

The safety shield system may then be removed from the pen injector 120 by unthreading the tubular rim portion 142 of the hub member 140 from the threaded tubular end portion 144 of the pen injector 120 and safely disposed of directly into a sharps container. Alternatively or in addition, the top 124 and bottom 193 caps can be re-installed over the shield 122 and hub members 140 to completely and safely encompass the needle cannula 134 as shown in FIG. 10. The first end 136 of the needle cannula 134 is thus safely received in the cup-shaped bottom cap 193 and the second end 138 of the needle cannula 134 is protected by the safety shield 122 and the top cap 124. The camming surfaces 197 and 185 interact to self-align the bottom cap and the top cap as they are re-attached to the pen needle.

Having described the embodiments of this invention, we now claim the invention, as follows.

What is claimed is:

1. A safety shield system for use with a body having fluid disposed therein, the safety shield system including:
   a hub member adapted to receive the body;
   a needle cannula mounted to the hub member and having a first end and a second end;
   a clip member attached to the hub member and having a lateral projection;
   a shield having an open end received around the clip member and a generally closed end having a central opening therethrough receiving the second end of the needle cannula, the shield being moveably mounted with respect to the hub member between a first position surrounding the needle cannula and a second position exposing the needle cannula, the shield including at least one opening for receiving the lateral projection when the shield is first retracted to the second position to expose the needle cannula and then extended to the first position surrounding the needle cannula such that the lateral projection locks the shield in the first position to prevent subsequent movement of the shield from the first position to the second position;
   a spring disposed within the shield for biasing the shield toward the first position; and
   a cap having a closed end and having means for non-removably securing the cap over the open end of the shield following use of the safety shield system to prevent re-use thereof.

2. The safety shield system defined in claim 1 wherein the lateral projection is made of a resilient material and includes a hook-shaped end portion opening toward the shield and the opening extends through a side wall of the shield for receiving the hook-shaped end portion therethrough to lock the shield in the first position surrounding the needle cannula.

3. The safety shield system defined in claim 1 wherein the clip member includes a plurality of spaced resilient lateral projections and the shield includes a plurality of corresponding openings through side walls of the shield for receiving the fingers and locking the shield in the first position surrounding the needle cannula.

4. The safety shield system defined in claim 3 wherein the clip member includes a common base with each of the resilient lateral projections extending from the base.

5. The safety shield system defined in claim 4 wherein the spring is a spiral spring having one end abutting the common base and an opposed end biased against the shield.

6. The safety shield system defined in claim 1 wherein the needle cannula extends through the hub member to define a first end for extending into the body to puncture a closure in a container received in the body, and a second end extending into the shield.

7. The safety shield system defined in claim 1 wherein the lateral projection includes a hook-shaped end portion which is larger than the opening in the shield such that the resilient lateral projection initially slides over the opening when the shield is retracted to the second position.

8. The safety shield system defined in claim 7 wherein the opening includes a chamfer with the lateral projection first engaging the chamfer and then extending into the opening when the shield returns to the first position from the second position.

9. The safety shield system defined in claim 7 wherein the shield includes at least one radial groove and the hub member includes at least one radially extending rib disposed within the groove to prevent rotation of the shield relative to the clip member.

10. The safety shield system defined in claim 7 wherein the shield includes a plurality of spaced radial grooves and the hub member includes a plurality of spaced radially extending ribs with a corresponding rib disposed within each groove to prevent rotation of the shield relative to the clip member.

11. The safety shield system as defined in claim 1 wherein the cap includes inwardly projecting ribs which are disposed within the grooves of the shield for preventing retraction of the shield relative to the hub member when the cap is received over the shield.

12. The safety shield system defined in claim 11 wherein the cap includes at least one first internal tab which engages the ribs of the hub member to secure the cap to the hub member and provide a degree of resistance during removal of the cap from the hub member.

13. The safety shield system defined in claim 11 further including a removable cup-shaped bottom cap initially received over the hub member opposite the top cap.

14. The safety shield system defined in claim 13 wherein the bottom cap interengages the top cap when the top cap is received over the shield and the bottom cap is received over the hub member thereby forming a sterile barrier.

15. The safety shield system defined in claim 14 wherein the top cap includes at least one second internal tab which engages the bottom cap to secure the bottom cap to the top cap and provide a degree of resistance during removal of the bottom cap from the top cap.

16. The safety shield system defined in claim 14 wherein the top cap includes a first camming surface and the bottom cap includes a second camming surface with the first and second camming surfaces abutting each other during rotation of the bottom cap relative to the top cap such that the bottom cap simultaneously moves axially away from the top cap.

17. The safety shield system defined in claim 1 further including a removable cup shaped top cap initially received over the shield and a removable cup-shaped bottom cap initially received over the hub member opposite the top cap to completely surround the needle cannula.

18. A pen needle and safety shield system for use with a container having fluid disposed therein, the pen needle and safety shield system comprising:

a pen injector having a body portion for receiving the container;

a hub member removably mounted to the body portion;

a needle cannula mounted to and extending through the hub member having a first end extending into the body portion for fluid communication with the container, and a second end extending away from the body portion for injection and transfer of the fluid from the container to a user;

a clip member mounted to the hub member and having a plurality of spaced resilient lateral projections;

a shield having an open end received around the clip member and a generally closed end having a central opening therethrough receiving the second end of the needle cannula, the shield being moveably mounted with respect to the hub member between a first position surrounding the second end of the needle cannula and a second position exposing the second end of the needle cannula, the shield including a plurality of openings for receiving the lateral projections when the shield is first retracted to the second position to expose the needle cannula and then extended to the first position surrounding the needle cannula such that the lateral projections lock the shield in the first position to prevent subsequent movement of the shield from the first position to the second position;

a spring disposed within the shield for biasing the shield toward the first position; and a cap having a closed end and having means for non-removably securing the cap over the open end of the shield following use of the pen needle and safety shield system to prevent re-use thereof.

19. The pen needle and safety shield system defined in claim 18 wherein the resilient lateral projections each include a hook-shaped end portion opening toward the shield and the openings extend through a side wall of the shield for receiving the hook-shaped end portions therethrough to lock the shield in the first position surrounding the needle cannula.

20. The pen needle and safety shield system defined in claim 18 wherein the resilient lateral projections each includes a hook-shaped end portion which is larger than the openings in the shield such that the resilient lateral projections initially slide over the openings when the shield is retracted to the second position.

21. The pen needle and safety shield system defined in claim 20 wherein the openings each includes a chamfer with the projections first engaging the chamfers and then extending into the openings when the shield returns to the first position from the second position.

22. The pen needle and safety shield system defined in claim 20 wherein the shield includes a plurality of spaced radial grooves and the hub member includes a plurality of spaced radially extending ribs with a corresponding rib disposed within each groove to prevent rotation of the shield relative to the clip member.

23. The pen needle and safety shield system as defined in claim 18 wherein the cap includes inwardly projecting ribs which are disposed within the grooves of the shield for preventing retraction of the shield relative to the hub member when the cap is received over the shield.

24. The pen needle and safety shield system defined in claim 23 wherein the cap includes a plurality of first internal tabs which engage the ribs of the hub member to secure the cap to the hub member and provide a degree of resistance during removal of the cap from the hub member.

25. The pen needle and safety shield system defined in claim 23 further including a removable cup-shaped bottom cap initially received over the hub member opposite the top cap.

26. The pen needle and safety shield system defined in claim 25 wherein the bottom cap interengages the top cap when the top cap is received over the shield and the bottom cap is received over the hub member.

27. The pen needle and safety shield system defined in claim 26 wherein the top cap includes a plurality of second internal tabs which engage the bottom cap to secure the bottom cap to the top cap and provide a degree of resistance during removal of the bottom cap from the top cap.

28. The safety shield system defined in claim 27 wherein the top cap includes a first camming surface and the bottom cap includes a second camming surface with the first and second camming surfaces abutting each other during rotation of the bottom cap relative to the top cap such that the bottom cap simultaneously moves axially away from the top cap.

* * * * *